United States Patent
Chang et al.

(10) Patent No.: US 9,478,023 B2
(45) Date of Patent: Oct. 25, 2016

(54) METHOD FOR DISCRIMINATING BETWEEN BACKGROUND AND TISSUE OF INTEREST, AND METHOD AND APPARATUS FOR GENERATING PHOTO-ACOUSTIC IMAGES FOR DETECTING CALCIFIED TISSUE

(71) Applicant: INDUSTRY-UNIVERSITY COOPERATION FOUNDATION SOGANG UNIVERSITY, Seoul (KR)

(72) Inventors: Jin Ho Chang, Seoul (KR); Jeeun Kang, Seoul (KR); Tai-Kyong Song, Seoul (KR); Yang Mo Yoo, Gyeonggi-do (KR)

(73) Assignee: INDUSTRY-UNIVERSITY COOPERATION FOUNDATION SOGANG UNIVERSITY, Seoul (KR)

( * ) Notice: Subject to any disclaimer, the term of this patent is extended or adjusted under 35 U.S.C. 154(b) by 133 days.

(21) Appl. No.: 14/399,748

(22) PCT Filed: Dec. 12, 2012

(86) PCT No.: PCT/KR2012/010770
§ 371 (c)(1),
(2) Date: Mar. 24, 2015

(87) PCT Pub. No.: WO2013/168873
PCT Pub. Date: Nov. 14, 2013

(65) Prior Publication Data
US 2015/0221081 A1    Aug. 6, 2015

(30) Foreign Application Priority Data

May 9, 2012    (KR) .................. 10-2012-0049290

(51) Int. Cl.
*G06K 9/00*    (2006.01)
*G06T 7/00*    (2006.01)
(Continued)

(52) U.S. Cl.
CPC .......... *G06T 7/0012* (2013.01); *A61B 5/0095* (2013.01); *G06K 9/00147* (2013.01);
(Continued)

(58) Field of Classification Search
None
See application file for complete search history.

(56) References Cited

U.S. PATENT DOCUMENTS

| | | | | |
|---|---|---|---|---|
| 6,081,740 | A * | 6/2000 | Gombrich | A61B 5/0071 600/117 |
| 6,505,060 | B1 * | 1/2003 | Norris | A61B 5/14551 600/323 |

(Continued)

FOREIGN PATENT DOCUMENTS

| | | |
|---|---|---|
| KR | 20080005747 | 1/2008 |
| KR | 20090087895 | 8/2009 |

(Continued)

OTHER PUBLICATIONS

Pai-Chi Li, Chen-Wei Wei, and Yae-lin Sheu, "Subband photoacoustic imaging for contrast improvement," Opt. Express 16, 20215-20226 (2008).*

(Continued)

*Primary Examiner* — Vu Le
*Assistant Examiner* — Samah Beg
(74) *Attorney, Agent, or Firm* — J. Rodman Steele, Jr.; Gregory M. Lefkowitz; Duane Morris LLP

(57) ABSTRACT

Provided is a method for discriminating a tissue of interest and a method for generating photo-acoustic images to detect a calcified tissue, which includes: detecting an intensity of each pixel of a tissue-of-interest image obtained for each wavelength; matching an index corresponding to an image, which has a greatest intensity corresponding to each pixel, to each pixel; generating a signal weight corresponding to each pixel in consideration of a wavelength absorbed by the tissue of interest; and applying the generated signal weight of each pixel to each pixel of an image obtained with a wavelength, which is the most absorbed by the tissue of interest, to generate an image in which a background is discriminated.

12 Claims, 13 Drawing Sheets

(51) Int. Cl.
- *A61B 5/00* (2006.01)
- *G06K 9/46* (2006.01)
- *G06K 9/52* (2006.01)
- *G06K 9/62* (2006.01)
- *G06K 9/20* (2006.01)

(52) U.S. Cl.
CPC ............... *G06K9/2018* (2013.01); *G06K 9/46* (2013.01); *G06K 9/52* (2013.01); *G06K 9/6201* (2013.01); *G06T 7/0081* (2013.01); *G06K 2009/4666* (2013.01); *G06T 2207/20144* (2013.01); *G06T 2207/30004* (2013.01)

(56) References Cited

U.S. PATENT DOCUMENTS

| | | | | |
|---|---|---|---|---|
| 8,045,153 B2* | 10/2011 | Mimura | ............. | G01N 21/6458 356/317 |
| 8,131,349 B2* | 3/2012 | Okawa | ............... | A61B 1/00096 600/477 |
| 8,140,139 B2* | 3/2012 | Grata | .................... | A61B 5/1112 600/310 |
| 8,175,669 B2* | 5/2012 | Kobayashi | ......... | A61B 5/14551 600/324 |
| 2001/0047137 A1* | 11/2001 | Moreno | ............... | A61B 5/0075 600/475 |
| 2004/0208385 A1* | 10/2004 | Jiang | .................... | A61B 5/0059 382/254 |
| 2008/0009748 A1* | 1/2008 | Gratton | ................ | A61B 5/0059 600/475 |
| 2012/0061590 A1* | 3/2012 | Khojasteh | ............ | A61B 1/0638 250/459.1 |

FOREIGN PATENT DOCUMENTS

| | | |
|---|---|---|
| KR | 100922784 | 10/2009 |
| KR | 20100120815 | 11/2010 |

OTHER PUBLICATIONS

Stetson et al. "Lesion contrast enhancement in medical ultrasound imaging", IEEE Transactions on Medical Imaging 16(4):416-25, Aug. 1997.*

Emelianov et al. "Synergy and Applications of Combined Ultrasound, Elasticity, and Photoacoustic Imaging", IEEE 2006, p. 405-415.*

* cited by examiner

METHOD FOR DISCRIMINATING BETWEEN BACKGROUND AND TISSUE OF INTEREST, AND METHOD AND APPARATUS FOR GENERATING PHOTO-ACOUSTIC IMAGES FOR DETECTING CALCIFIED TISSUE

CROSS-REFERENCE TO RELATED APPLICATIONS

This application is a §371 national stage entry of International Application No. PCT/KR2012/010770, flied Dec. 13, 2012, which claims priority to South Korean Patent Application Nos. 10-2012-0049290 filed May 9, 2012, the entire contents of which are incorporated herein by reference.

TECHNICAL FIELD

The present disclosure relates to a method for discriminating between a background and a tissue of interest, and more particularly, to a method and apparatus for discriminating a tissue of interest, in which a photo-acoustic image obtained while changing an optical wavelength is analyzed to endow an index to each pixel of the image, and a background signal and a signal to be obtained are discriminated by using the endowed index.

In addition, the present disclosure relates to a method and apparatus for generating photo-acoustic images, which allows easy discrimination between a calcified tissue and surrounding tissues in a human body.

BACKGROUND ART

Various human tissues appearing in a photo-acoustic image have different optical absorption coefficients from each other.

FIG. 1 shows an optical absorption coefficient in a human tissue.

Referring to FIG. 1, each material has a given optical wavelength to output an optimal photo-acoustic coefficient (absorption coefficient) in a human body. For example, Hb shows an optimal optical absorption coefficient near 400 nm and 550 nm, $HbO_2$ and protein shows an optimal optical absorption coefficient near 420 nm, 550 nm and 900 nm, and protein shows an optimal optical absorption coefficient near 200 nm. By discriminating an optical wavelength with an optimal optical absorption coefficient by using such different optical absorption coefficients of materials, a surrounding background and a physiological change of a human body of interest may be discriminated.

If a photo-acoustic imaging technique using an optical absorption coefficient in a human tissue is used, a physiological change in the human body may be imaged using a variation according to each optical wavelength. Meanwhile, even though all tissues react optimally to specific optical wavelengths, they may also react, though not optimal, when imaging another tissue. In other words, all optical absorption coefficients may not be perfectly discriminated, and thus there is needed a method and apparatus for selectively discriminating a background.

Moreover, calcification in the breast and thyroid tissues becomes an important clue in an early diagnosis of cancer. In other words, calcification of a micro scale plays a role of an indicator of cancer occurrence, and thus it is very important to detect a calcified tissue in advance.

An early diagnosis of breast cancer and thyroid cancer is performed by checking calcification by means of mammography or verifying a positive or negative reaction by means of ultrasonic image and biopsy.

In case of the mammography, however, X-ray is excessively irradiated to a human body, a pain caused by compressing is applied to the patient, real-time imaging is not easy, and particularly it is not easily applied to thyroid.

Meanwhile, the ultrasonic image is a non-radiological imaging method which may give an image in real time, and any inconvenience such as compressing is not given to the patient. However, due to low contrast and serious noise in the image, identifiability deteriorates, and thus when guiding a biopsy needle, it is not easy to check an accurate location of a calcified tissue or lesion. Therefore, there is needed a real-time imaging technique capable of further emphasizing an image of a micro-calcified tissue and minimizing a reaction of an image without a calcified tissue.

DISCLOSURE

Technical Problem

A first object of the present disclosure is to provide a method for discriminating a tissue of interest, which may analyze a photo-acoustic image obtained while changing an optical wavelength to endow an index to each pixel of the image, and then discriminating between a background signal and a signal to be obtained by using the endowed index.

A second object of the present disclosure is to provide an apparatus for discriminating a tissue of interest, which may show only a target to be observed with a higher contrast resolution.

Moreover, a third object of the present disclosure is to provide a method for generating photo-acoustic images, which may allow easy discrimination between a calcified tissue and surrounding tissues in a human body.

A fourth object of the present disclosure is to provide an apparatus for generating photo-acoustic images, which may allow easy discrimination between a clinically meaningful calcified tissue and a meaningless calcified tissue not observed even by mammography.

In addition, the present disclosure is directed to providing a computer-readable medium in which a program for executing the above method in a computer is recorded.

Technical Solution

In a first embodiment to accomplish the first object, the present disclosure provides a method for discriminating a tissue of interest, which includes: detecting an intensity of each pixel of a tissue-of-interest image obtained for each wavelength; matching an index corresponding to an image, which has a greatest intensity corresponding to each pixel, to each pixel; generating a signal weight corresponding to each pixel in consideration of a wavelength absorbed by the tissue of interest; and applying the generated signal weight of each pixel to each pixel of an image obtained with a wavelength, which is the most absorbed by the tissue of interest, to generate an image in which a background is discriminated.

According to an embodiment of the present disclosure, a signal weight of a pixel corresponding to an index of a wavelength, at which an optical absorption coefficient of the tissue of interest and an optical absorption coefficient of a surrounding tissue are the most different from each other, may be selected as a greatest value.

In other words, a signal weight of a pixel corresponding to an index of a wavelength, at which a difference between an optical absorption coefficient of the tissue of interest and an optical absorption coefficient of a surrounding tissue is maximum, may be selected as a greatest value even though the index is not an index of a wavelength at which optical energy is the most absorbed by the tissue of interest.

According to another embodiment of the present disclosure, a signal weight of a pixel corresponding to an index of a wavelength, which is the most absorbed by the tissue of interest, may be selected as a greatest value.

In addition, a signal weight of a pixel corresponding to an index of a wavelength, which is the second absorbed by the tissue of interest, may be set to be equal to or greater than 0 and smaller than a signal weight of the pixel corresponding to the index of a wavelength, which is the most absorbed by the tissue of interest.

In a second object to accomplish the first object, the present disclosure also provides a method for discriminating a tissue of interest, which includes: detecting an intensity of each pixel of a tissue-of-interest image obtained for each wavelength; generating a maximum/minimum ratio conversion weight, which is to be applied to each pixel, by using a ratio between a maximum value and a minimum value of the intensity corresponding to each pixel; and applying the generated maximum/minimum ratio conversion weight to each pixel of an image obtained with a wavelength, which is the most absorbed by the tissue of interest, to generate an image in which a background is discriminated.

In other words, pixels which do not change over a predetermined level according to a wavelength may be regarded as a background, and pixels of the tissue of interest will be included in pixels which change over a predetermined level according to a wavelength.

Therefore, when a difference between the maximum value and the minimum value is greater than a predetermined value, a maximum value of the maximum/minimum ratio conversion weight may be endowed, and when the difference between the maximum value and the minimum value is smaller than the predetermined value, a minimum value of the maximum/minimum ratio conversion weight may be endowed.

When detecting an intensity of each pixel while changing an optical wavelength, a pixel representing an intensity within a predetermined range and a pixel representing an intensity over the predetermined range may be discriminated for various wavelengths. A ratio of a maximum value and a minimum value of each pixel obtained while changing an optical wavelength may be matched with each pixel to configure a maximum/minimum frame, a maximum/minimum ratio conversion weight frame may be configured by using the ratio of a maximum value and a minimum value, and a tissue of interest and a background may be discriminated by detecting a pixel representing an intensity over the predetermined range.

In a third embodiment to accomplish the first object, the present disclosure provides a method for discriminating a tissue of interest, which includes: detecting an intensity of each pixel of a tissue-of-interest image obtained for each wavelength; matching an index corresponding to an image, which has a greatest intensity corresponding to each pixel, to each pixel; generating a signal weight corresponding to each pixel in consideration of a wavelength absorbed by the tissue of interest; generating a maximum/minimum ratio conversion weight, which is to be applied to each pixel, by using a ratio between a maximum value and a minimum value of the intensity corresponding to each pixel; generating a final weight by using the signal weight and the maximum/minimum ratio conversion weight; and applying the generated final weight of each pixel to each pixel of an image obtained with a wavelength, which is the most absorbed by the tissue of interest, to generate an image in which a background is discriminated.

In a first embodiment to accomplish the second object, the present disclosure provides an apparatus for discriminating a tissue of interest, which includes: a pixel intensity detection unit configured to detect an intensity of each pixel of a tissue-of-interest image obtained for each wavelength; an index frame generation unit configured to match an index corresponding to an image, which has a greatest intensity corresponding to each pixel, to each pixel to generate an index frame; a signal weight generation unit configured to generate a signal weight corresponding to each pixel in consideration of a wavelength absorbed by the tissue of interest; and a weight applying unit configured to apply the generated signal weight of each pixel to each pixel of an image obtained with a wavelength, which is the most absorbed by the tissue of interest, to generate an image in which a background is discriminated.

In a second embodiment to accomplish the second object, the present disclosure provides an apparatus for discriminating a tissue of interest, which includes: a pixel intensity detection unit configured to detect an intensity of each pixel of a tissue-of-interest image obtained for each wavelength; a maximum/minimum ratio conversion weight generation unit configured to generate a maximum/minimum ratio conversion weight, which is to be applied to each pixel, by using a ratio between a maximum value and a minimum value of the intensity corresponding to each pixel; and a weight applying unit configured to apply the generated maximum/minimum ratio conversion weight to each pixel of an image obtained with a wavelength, which is the most absorbed by the tissue of interest, to generate an image in which a background is discriminated.

In a third embodiment to accomplish the second object, the present disclosure provides an apparatus for discriminating a tissue of interest, which includes a pixel intensity detection unit configured to detect an intensity of each pixel of a tissue-of-interest image obtained for each wavelength; an index frame generation unit configured to match an index corresponding to an image, which has a greatest intensity corresponding to each pixel, to each pixel to generate an index frame; a signal weight generation unit configured to generate a signal weight corresponding to each pixel in consideration of a wavelength absorbed by the tissue of interest; a maximum/minimum ratio conversion weight generation unit configured to generate a maximum/minimum ratio conversion weight, which is to be applied to each pixel, by using a ratio between a maximum value and a minimum value of the intensity corresponding to each pixel; a weight frame generation unit configured to generate a final weight by using the signal weight and the maximum/minimum ratio conversion weight to generate a weight frame; and a weight applying unit configured to apply the generated final weight of each pixel to each pixel of an image obtained with a wavelength, which is the most absorbed by the tissue of interest, to generate an image in which a background is discriminated.

In another aspect, the present disclosure provides a computer-readable recording medium, in which a program for executing the method for discriminating a tissue of interest as described above in a computer is recorded.

To accomplish the third object, the present disclosure provides a method for generating photo-acoustic images, which includes: applying optical energy having a specific wavelength to a target having a calcified tissue; receiving a photo-acoustic signal generated from the target; and generating a photo-acoustic image of the calcified tissue from the photo-acoustic signal.

According to an embodiment of the present disclosure, when the specific wavelength is in a range of 680 nm to 710 nm, a photo-acoustic image of the calcified tissue may be generated by using the fact that the calcified tissue generates a greater photo-acoustic signal in comparison to surrounding biological tissues.

According to another embodiment of the present disclosure, optical energy having two different wavelengths may be applied to the target, and a calcified tissue may be imaged by using each photo-acoustic signal generated from the target.

At this time, one wavelength may be present in a wavelength band of 680 nm to 710 nm, and the other wavelength may vary depending on an optical absorption coefficient the surrounding biological tissues.

In addition, by comparing magnitudes of photo-acoustic signals generated from the target, it is possible to remove a surrounding image other than the calcified tissue or reinforce the calcified tissue image.

According to another embodiment of the present disclosure, optical energy corresponding to a wavelength band of 680 nm to 710 nm may be applied to the target, a magnitude of the photo-acoustic signal generated from the target and optical energy corresponding to a wavelength band of 800 nm to 1000 nm may be applied to the target, and a calcified tissue may be discriminated in consideration of a ratio of the magnitude of the photo-acoustic signal generated from the target.

In addition, the method may further include: measuring a first photo-acoustic signal for micro calcification-active wavelength band; measuring a second photo-acoustic signal for a micro calcification-inactive wavelength band; and reinforcing the first photo-acoustic signal when the first photo-acoustic signal is greater than the second photo-acoustic signal and removing the second photo-acoustic signal when the first photo-acoustic signal is smaller than the second photo-acoustic signal.

In addition, the method may further include: measuring a first photo-acoustic signal for micro calcification-active wavelength band; measuring a second photo-acoustic signal for a micro calcification-inactive wavelength band; and comparing a first image generated from the first photo-acoustic signal with a second image generated from the second photo-acoustic signal to remove a signal which is found in both of them and generate an image of the calcified tissue by using a signal found only in the first image.

In order to accomplish the fourth object, the present disclosure provides an apparatus for generating photo-acoustic images, which includes: a photo-acoustic signal receiving unit configured to receive a photo-acoustic signal generated from a target; and a photo-acoustic image generation unit configured to generate a photo-acoustic image of a calcified tissue included in the target from the received photo-acoustic signal.

In another aspect, the present disclosure provides a computer-readable recording medium, in which a program for executing the method for generating photo-acoustic images as described above in a computer is recorded.

Advantageous Effects

According to the present disclosure, a photo-acoustic image obtained while changing an optical wavelength may be analyzed to endow an index to each pixel of the image, and a background signal and a signal to be obtained may be discriminated by using the endowed index. In addition, according to the present disclosure, a user may implement only a target to be observed with a higher contrast resolution. Further, according to the present disclosure, in a result image of a photo-acoustic experiment performed using a breast clinical specimen, a breast clinical specimen, a staple region for fixing the breast clinical specimen, and an interaction region between the clinical specimen and laser may be discriminated from each other.

In addition, according to the present disclosure, a calcified tissue and surrounding tissues in a human body may be easily discriminated. In addition, according to the present disclosure, a clinically meaningful calcified tissue and a meaningless calcified tissue not observed even by mammography may be classified. Further, according to the present disclosure, calcification of a micro scale in a breast or thyroid tissue may be detected in real time. Therefore, accurate information about a micro-calcified tissue may be provided to the user, and thus more accurate needle biopsy may be guided. Further, regarding a false positive problem which is always an issue in early diagnosis, more elaborate and reliable diagnosis may be ensured.

BEST MODEL

Figure 1:
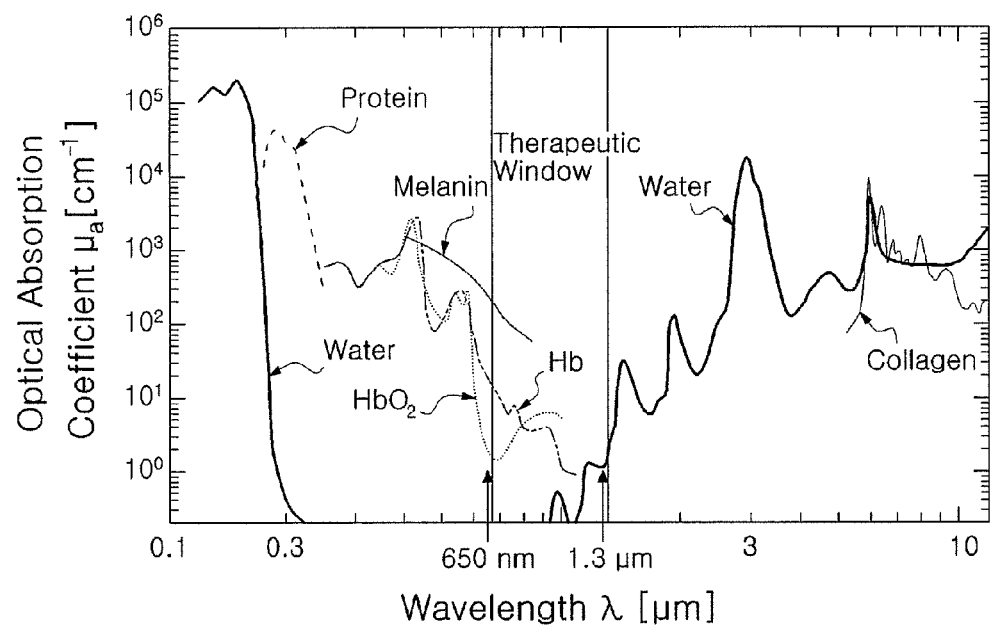
FIG. 1 shows an optical absorption coefficient in a human tissue.

Prior to the detailed description of the present disclosure, solutions of the present disclosure will be summarized and technical features of the present disclosure will be proposed.

A method for discriminating a tissue of interest according to an embodiment of the present disclosure includes: detecting an intensity of each pixel of a tissue-of-interest image obtained for each wavelength; matching an index corresponding to an image, which has a greatest intensity corresponding to each pixel, to each pixel; generating a signal weight corresponding to each pixel in consideration of a wavelength absorbed by the tissue of interest; and applying the generated signal weight of each pixel to each pixel of an image obtained with a wavelength, which is the most absorbed by the tissue of interest, to generate an image in which a background is discriminated.

Hereinafter, the embodiments of the present disclosure will be described in detail with reference to accompanying drawings so that the embodiments may be easily implemented by those skilled in the art. However, the present disclosure may be implemented in various ways without being limited to the embodiments, as obvious to those skilled in the art.

Exemplary embodiments now will be described more fully hereinafter with reference to the accompanying drawings, in which exemplary embodiments of the present disclosure are shown. In the drawings, like reference numerals denote like elements throughout the specification, and it is revealed that when a drawing is explained, another drawing may be cited together, if necessary. Moreover, when describing operation principles for the exemplary embodiments of the present disclosure, explanation about well-known functions or components as well as other relevant descriptions may be omitted to avoid unnecessarily obscuring the presented embodiments.

In addition, throughout the specification, when any portion is described as being 'connected' to another portion, this means not only a case where they are 'directly connected' but also a case where they are 'indirectly connected' with any element being interposed between them. In the specification, the singular forms "a", "an" and "the" are intended to include the plural forms as well, unless the context clearly indicates otherwise. It will be further understood that the term "comprises" or "comprising" when used in this specification, specifies the presence of stated features, steps, operations, and/or components, but do not preclude the presence or addition of one or more other features, steps, operations, and/or components.

In the present disclosure, it is assumed that the degree of reaction according to an optical wavelength of a tissue of interest, which is to be observed, is already known, as shown in FIG. 1.

Figure 2:
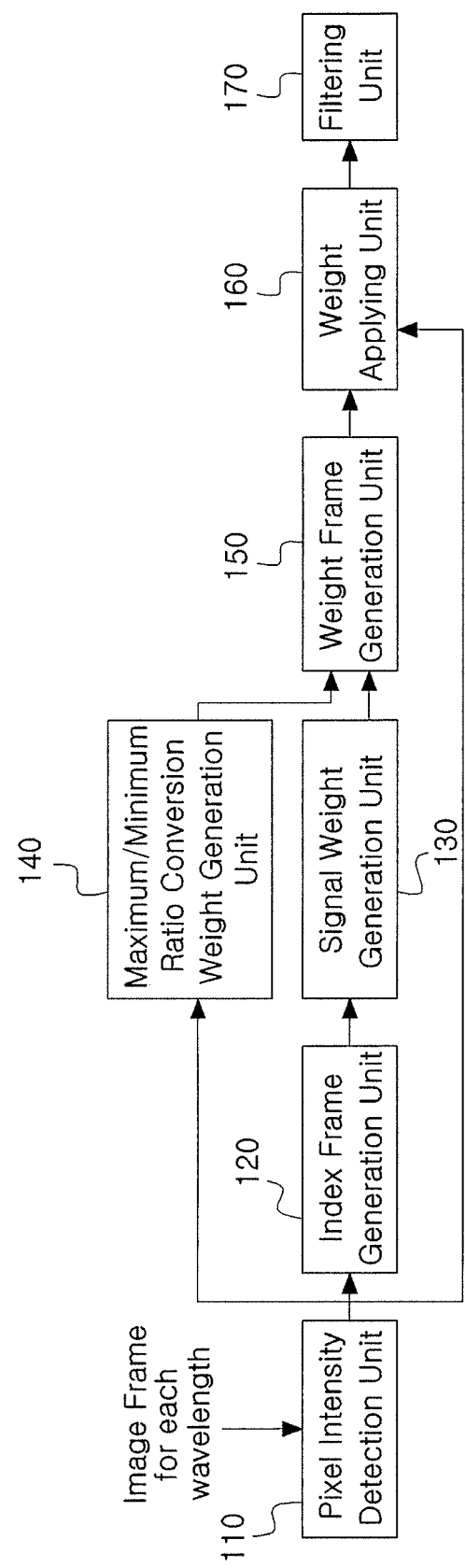
FIG. 2 is a diagram showing an apparatus for discriminating a tissue of interest according to a preferred embodiment of the present disclosure.

FIG. 2 is a diagram showing an apparatus for discriminating a tissue of interest according to a preferred embodiment of the present disclosure.

Referring to FIG. 2, an apparatus for discriminating a tissue of interest according to this embodiment includes a pixel intensity detection unit 110, an index frame generation unit 120, a signal weight generation unit 130, a maximum/minimum ratio conversion weight generation unit 140, a weight frame generation unit 150, a weight applying unit 160 and a filtering unit 170.

The pixel intensity detection unit 110 detects an intensity of each pixel of an image obtained for each wavelength and generates an image frame for each wavelength. At this time, the image frame may be an image frame in which an intensity corresponds to each pixel.

Meanwhile, the image used by the pixel intensity detection unit 110 to generate an image frame may be an envelope-detected magnitude signal, obtained by performing beam focusing to a photo-acoustic signal acquired for each wavelength, or a back-end processed image having a sufficiently adjusted dynamic range. When an image frame is generated with a magnitude signal, the amount of data to be processed may be large depending on a set ROI (region of interest) but ensures more stable performance. When an image frame is generated with a back-end processed image, the amount of data to be processed may be smaller in comparison to ROI, but the background discriminating performance may deteriorate depending on a set dynamic range.

The index frame generation unit 120 generates an index frame in which an index of an image frame, which has a greatest intensity corresponding to each pixel of image frames generated by the pixel intensity detection unit 110, corresponds to each pixel thereof. At this time, an index is matched with every wavelength, and the index of the image frame may be identical to the index of the wavelength.

The index frame generation unit 120 generates an index corresponding to an optimal optical absorption coefficient for each pixel of the image frames generated by the pixel intensity detection unit 110.

A case where an N number of wavelength regions representing a tissue of interest in a best way may be mathematically expressed as follows.

$$\lambda = [\lambda_1, \lambda_2, \lambda_3, \lambda_4, \ldots, \lambda_N]$$ Equation 1

Indexes 1, 2, 3, ..., N are endowed to the N number of wavelength regions.

The signal weight generation unit 130 configures a signal weight frame for each pixel by applying a great signal weight to an index, which is to be highlighted, and a small signal weight to an index, which is to be discriminated, among indexes included in the index frame generated by the index frame generation unit 120.

In an embodiment, the signal weight generation unit 130 may set a signal weight of a pixel corresponding to an index of wavelength, at which an optical absorption coefficient of the tissue of interest and an optical absorption coefficient of a surrounding tissue are the most different from each other, as a greatest value.

In other words, a signal weight of a pixel corresponding to an index of a wavelength, at which a difference between an optical absorption coefficient of the tissue of interest and an optical absorption coefficient of a surrounding tissue is maximum, is selected as a greatest value even though the index is not an index of a wavelength at which optical energy is the most absorbed by the tissue of interest.

In another embodiment, among the indexes included in the index frame generated by the index frame generation unit 120, the signal weight generation unit 130 sets a signal weight of a pixel corresponding to an index of a wavelength, which is the most absorbed by the tissue of interest, to be 1 and also sets a signal weight of a pixel corresponding to an index of another wavelength to be a value equal to or greater than 0 and smaller than 1. At this time, it is assumed that the wavelength at which a difference between an optical absorption coefficient of the tissue of interest and an optical absorption coefficient of a surrounding tissue is maximum is already know, as shown in FIG. 1.

For example, in the optical absorption coefficient of each wavelength, depicted in FIG. 1, if a tissue shows great optical absorption coefficients at two or more wavelengths, a weight of a pixel corresponding to an index corresponding to a wavelength showing a greatest optical absorption coefficient may be set to be 1, and a weight of a pixel corresponding to an index corresponding to a wavelength showing a next greatest optical absorption coefficient may be set to be ½.

Meanwhile, a weight of a pixel corresponding to an index of a wavelength, at which an optical absorption coefficient of the tissue of interest and an optical absorption coefficient of a surrounding tissue are the most different from each other, may be set to be 0, and a weight of a pixel corresponding to an index of another wavelength may be set to be a value greater than 0 and equal to or smaller than 1. However, the method for determining a signal weight is not limited thereto.

If a weight of a pixel corresponding to an index of a wavelength, which is the most absorbed by the tissue of interest, is set to be 1, the tissue-of-interest image has a greater intensity in comparison to a background tissue image. However, if a weight of a pixel corresponding to an index of a wavelength, which is the most absorbed by the tissue of interest, is set to be 1, the background tissue image will have a greater intensity in comparison to the image of the tissue of interest. Therefore, by suitably adjusting a weight of a pixel corresponding to an index of a wavelength, it is possible to easily discriminate between an optimal tissue of interest and a background tissue.

The maximum/minimum ratio conversion weight generation unit 140 configures a maximum/minimum ratio conversion weight frame by determining a maximum/minimum ratio conversion weight using a ratio between a minimum value and a maximum value at each pixel.

The maximum/minimum ratio conversion weight generation unit 140 extracts a maximum value and a minimum value of an intensity corresponding to each pixel, among the image frames generated by the pixel intensity detection unit 110, for each pixel and then generates a maximum/minimum ratio conversion weight equal to or greater than 0 and smaller than 1 according to a difference between the maximum value and the minimum value.

For example, if a pixel may be determined as a pixel of the tissue of interest when the difference between the maximum value and the minimum value is great, a maximum value of the maximum/minimum ratio conversion weight is endowed, and if a pixel may be determined as a pixel of a background when the difference between the maximum value and the minimum value is small, a minimum value of the maximum/minimum ratio conversion weight may be endowed. Meanwhile, for a pixel of a tissue other than the tissue of interest or the background, a maximum/minimum ratio conversion weight between 0 and 1 may be endowed.

The maximum/minimum ratio conversion weight generation unit 140 may set the maximum/minimum ratio conversion weight to be 0 in order to discriminate a signal (static signal) whose intensity changes small with respect to all wavelengths, and may also set the maximum/minimum ratio conversion weight to be 1 in order to highlight a background image in comparison to the tissue-of-interest image. Depending on a tissue which is to remain, only the background may be left, and depending on a configuration setting of the index frame generation unit 120, a modification may also be available to find a portion representing a minimum reaction.

The weight frame generation unit 150 generates a final weight by using the signal weight generated by the signal weight generation unit 130 and the maximum/minimum ratio conversion weight generated by the maximum/minimum ratio conversion weight generation unit 140. For example, a final weight may be generated by multiplying the signal weight of the signal weight generation unit 130 by the maximum/minimum ratio conversion weight of the maximum/minimum ratio conversion weight generation unit 140 for each corresponding pixel.

As a result, a final weight frame is configured by using the signal weight frame obtained from the index frame and the maximum/minimum ratio conversion weight frame obtained from the maximum value and the minimum value of each intensity of pixel.

The weight applying unit 160 applies the weight generated by the weight frame generation unit 150 to the image frame generated from a wavelength corresponding to a greatest optical absorption coefficient of the tissue of interest. By applying the weight to the image frame, the background image becomes dark, and the image of the tissue of interest becomes bright.

In other words, the weight applying unit 160 discriminates a background by masking the image frame configured with the optimal wavelength by using the weight generated by the weight frame generation unit 150. As a result, in a photo-acoustic imaging technique, a reaction according to the change of wavelength of light of a specific tissue may be analyzed and a high contrast image may be provided to the corresponding tissue.

The filtering unit 170 removes noise by filtering the image frame output from the weight applying unit 160. The filtering unit 170 performs 2-D LPF to the image frame in order to improve a combination of the image frame output from the weight applying unit 160 with an ultrasonic image as well as image quality.

Figure 3:
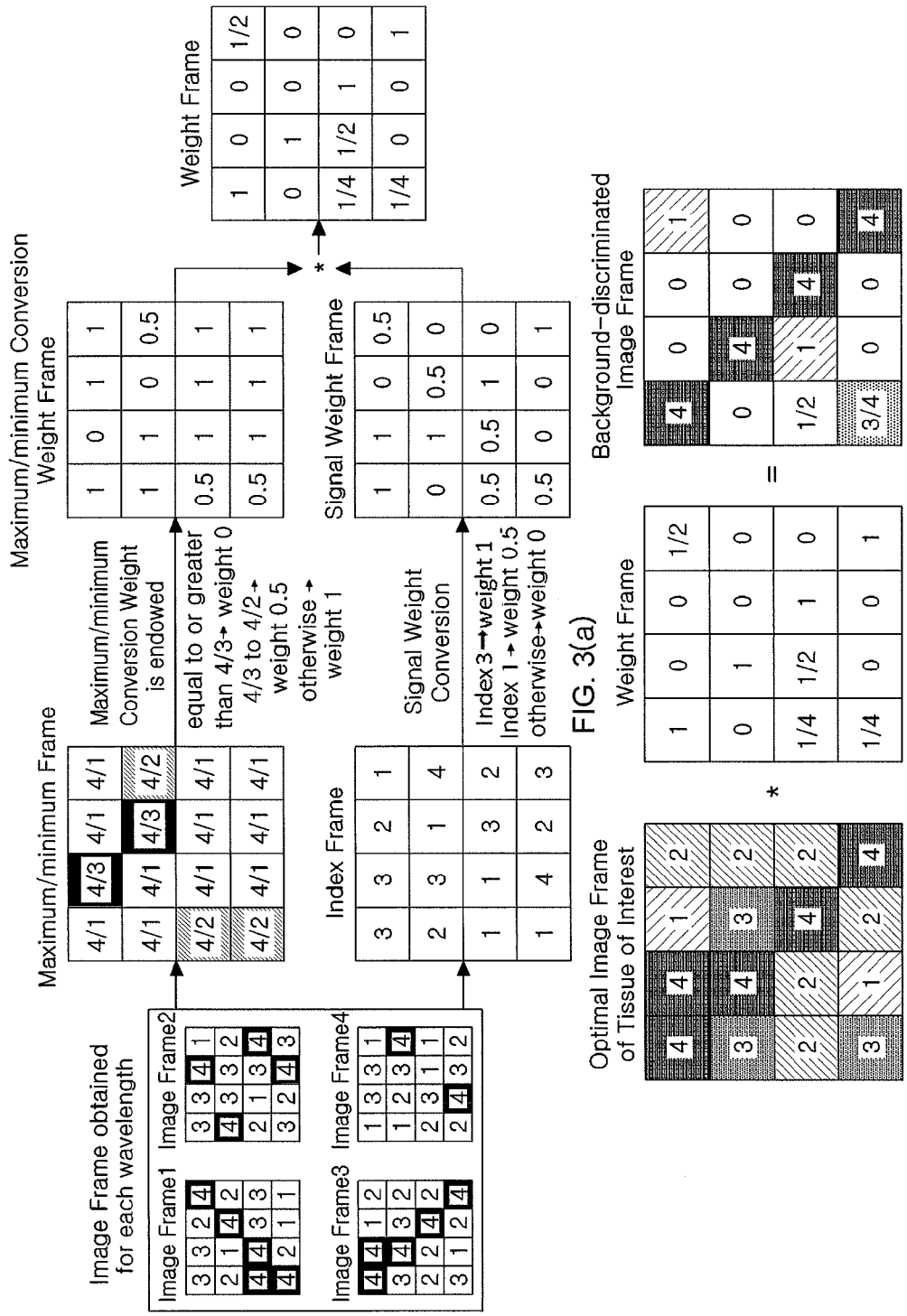
FIGS. 3a and 3b illustrate a process of generating an index frame, a signal weight frame, a maximum/minimum ratio conversion weight frame and a final weight frame according to an embodiment of the present disclosure.

FIG. 3 illustrates a process of generating an index frame, a signal weight frame, a maximum/minimum ratio conversion weight frame and a final weight frame according to an embodiment of the present disclosure.

Referring to FIGS. 2 and 3(a), image frames obtained by the pixel intensity detection unit 110 for each wavelength are expressed as image frame 1, image frame 2, image frame 3, and image frame 4.

From the image frames, the index frame generation unit 120 generates an index frame in which an index of an image frame having a greatest intensity corresponding to each pixel is matched to each pixel. The signal weight generation unit 130 generates a signal weight frame by converting the signal weight by using the index frame.

For example, if an index corresponding to the optimal wavelength is 3 and the wavelength corresponding to an index 1 has an intensity the second greater than the optimal wavelength with respect to the tissue of interest, the signal weight may be converted as follows. In other words, a signal weight of 1 is allocated to the pixel having an index of 3, a signal weight of 0.5 is allocated to the pixel having an index of 2, and a signal weight of 0 is allocated to other pixels.

Meanwhile, the maximum/minimum ratio conversion weight generation unit 140 generates a ratio between a minimum value and a maximum value at each pixel from the image frames obtained by the pixel intensity detection unit 110 for each wavelength, and generates a maximum/minimum ratio conversion weight from the ratio. The maximum/ minimum ratio conversion weight may be converted as follows. For example, 0 is endowed to a pixel having a maximum value/minimum value ratio close to 1, and 1 is endowed to a pixel having a maximum value/minimum value ratio close to 0. In FIG. 3, 0 is endowed when the maximum value/minimum value ratio is equal to or greater than 4/3, 0.5 is endowed when the maximum value/minimum value ratio is between 4/3 and 4/2, and 1 is endowed when the maximum value/minimum value ratio is smaller than 4/2.

Next, the weight frame generation unit 150 generates a final weight by using the signal weight of the signal weight generation unit 130 and the maximum/minimum ratio conversion weight of the maximum/minimum ratio conversion weight generation unit 140. It can be found that a weight frame is generated by multiplying the weight frame and the signal weight frame for each pixel.

Finally, referring to FIG. 3(*b*), the weight applying unit 160 generates an image frame in which a background is discriminated, by multiplying the image frame 3 corresponding to the optimal wavelength by the weight frame for each pixel.

Figure 4:
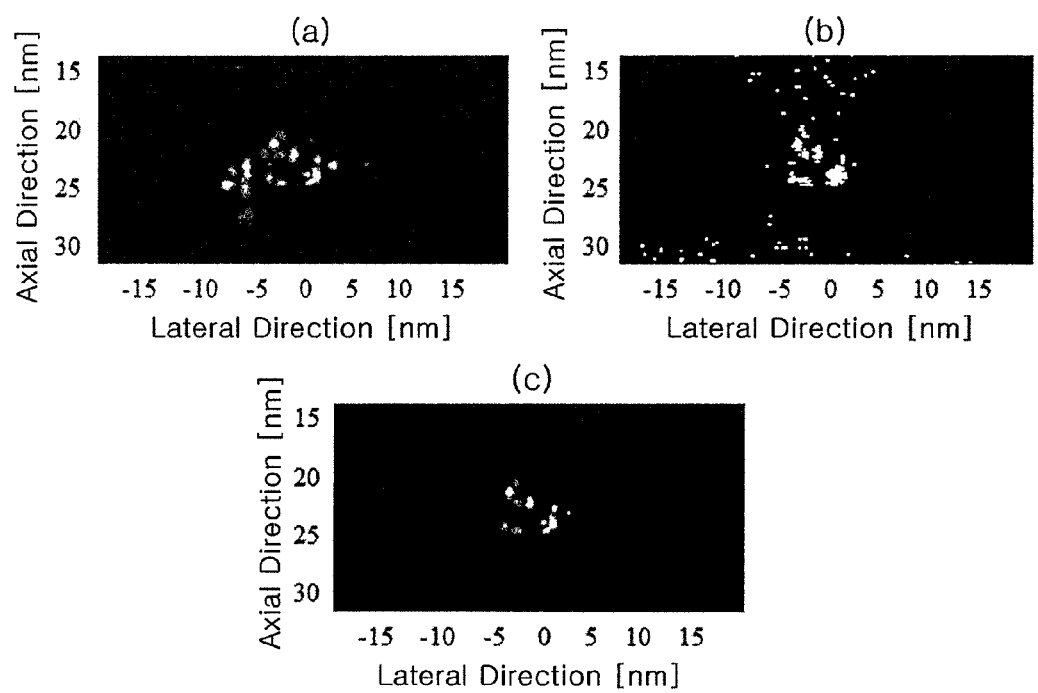
FIGS. 4a, 4b and 4c show a photo-acoustic image of breast biopsy tissue including micro calcification, a weight frame therefor, and a result obtained by image LPF (median filtering) after masking, respectively.

FIG. 4 shows a photo-acoustic image of a breast biopsy tissue including micro calcification, a weight frame therefor, and a result obtained by image LPF (median filtering) after masking, respectively.

FIG. 4(*a*) shows a photo-acoustic image of a breast biopsy tissue having micro calcification, FIG. 4(*b*) shows a weight frame of a breast biopsy tissue having micro calcification, and 4(*c*) shows a result obtained by performing image LPF (median filtering) after masking.

The image is obtained by applying optical energy of 19 mJ/cm² with a Surelite OPO system (Continuum, USA) and then performing an experiment with SonixTouch (Ultrasonix, Canada) to which a research package SonixDAQ is mounted. The experiment was performed while changing the wavelength from 680 nm to 750 nm by 10 nm each, and then changing the wavelength from 800 nm to 1000 nm by 50 nm each. The breast biopsy tissue having micro calcification is fixed using a stapler, and the stapler mostly has an optimal wavelength of 800 to 1000 nm.

When a signal weight frame is generated from the index frame, a weight of 16 was given to an index 2 having an optimal wavelength of 700 nm, which is an optimal wavelength of the micro calcification, and a weight of 0 was given to other indexes. The maximum/minimum ratio conversion weight frame is masked to be 0 if the maximum value/minimum value is smaller than 1.

Figure 5:
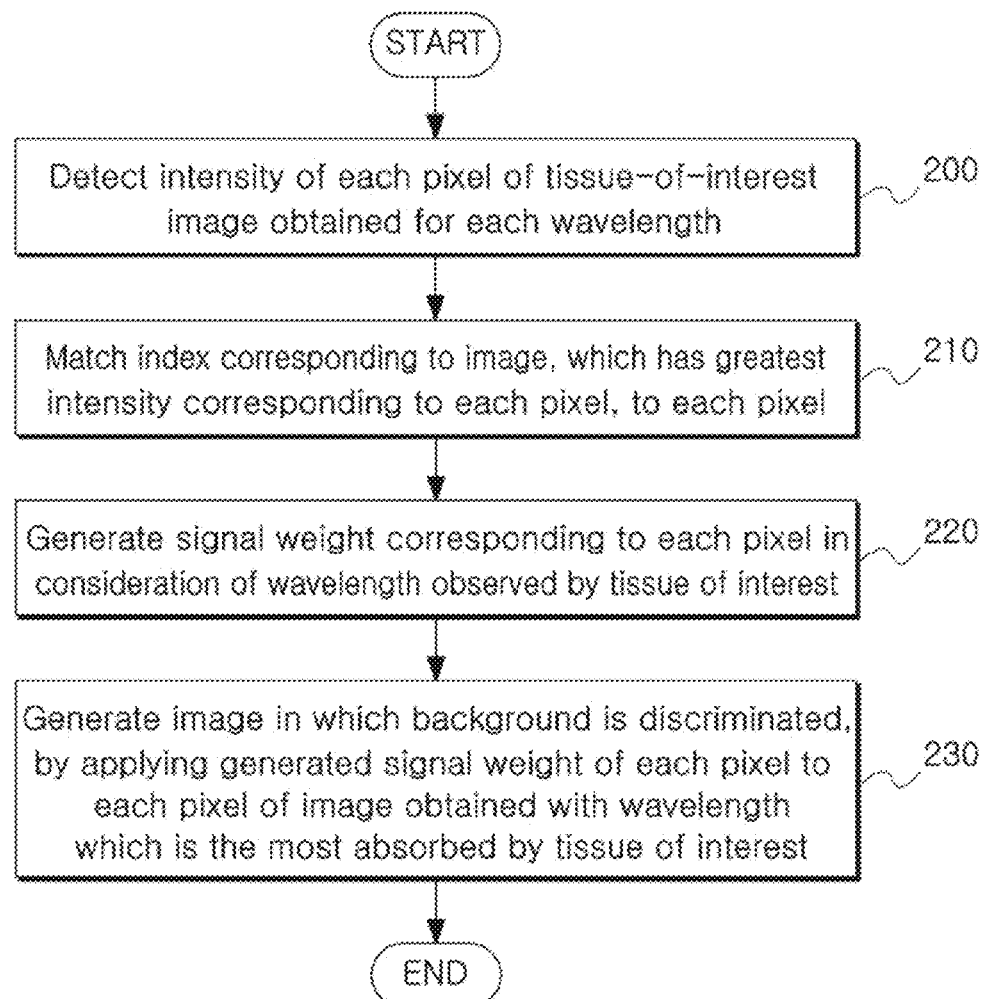
FIG. 5 is a flowchart for illustrating a method for discriminating a tissue of interest according to a preferred embodiment of the present disclosure.

FIG. 5 is a flowchart for illustrating a method for discriminating a tissue of interest according to a preferred embodiment of the present disclosure.

Referring to FIG. 5, a method for discriminating a tissue of interest according to this embodiment includes processes time-sequentially performed by the apparatus for discriminating a tissue of interest, depicted in FIG. 2. Therefore, even though not described in detail below, the features described above in relation to the apparatus for discriminating a tissue of interest, depicted in FIG. 2, are also applied to the method for discriminating a tissue of interest according to this embodiment.

In Step 200, the apparatus for discriminating a tissue of interest detects an intensity of each pixel of a tissue-of-interest image obtained for wavelength. By using the intensity detected for each pixel, an image frame may be generated for each wavelength. At this time, the image frame may be an image frame in which an intensity corresponds to each pixel.

In Step 210, the apparatus for discriminating a tissue of interest matches an index corresponding to an image, which has a greatest intensity corresponding to each pixel, to each pixel. At this time, the index is matched with every wavelength, and the index of the image or the image frame may be identical to the index of the wavelength.

In Step 220, the apparatus for discriminating a tissue of interest generates a signal weight corresponding to each pixel in consideration of a wavelength absorbed by the tissue of interest.

At this time, a signal weight of a pixel corresponding to an index of wavelength, in which an optical absorption coefficient of the tissue of interest and an optical absorption coefficient of the surrounding tissue are the most different from each other, may be set as a greatest value.

In another example, a signal weight of a pixel corresponding to an index of wavelength, which is the most absorbed by the tissue of interest, may be set as a greatest value. In addition, a signal weight of a pixel corresponding to an index of wavelength, which is the second absorbed by the tissue of interest, may be set to be greater than 0 and smaller than a signal weight of the pixel corresponding to the index of a wavelength, which is the most absorbed by the tissue of interest.

In Step 230, the apparatus for discriminating a tissue of interest generates an image in which a background is discriminated, by applying the generated signal weight of each pixel to each pixel of an image obtained with a wavelength, which is the most absorbed by the tissue of interest.

Figure 6:
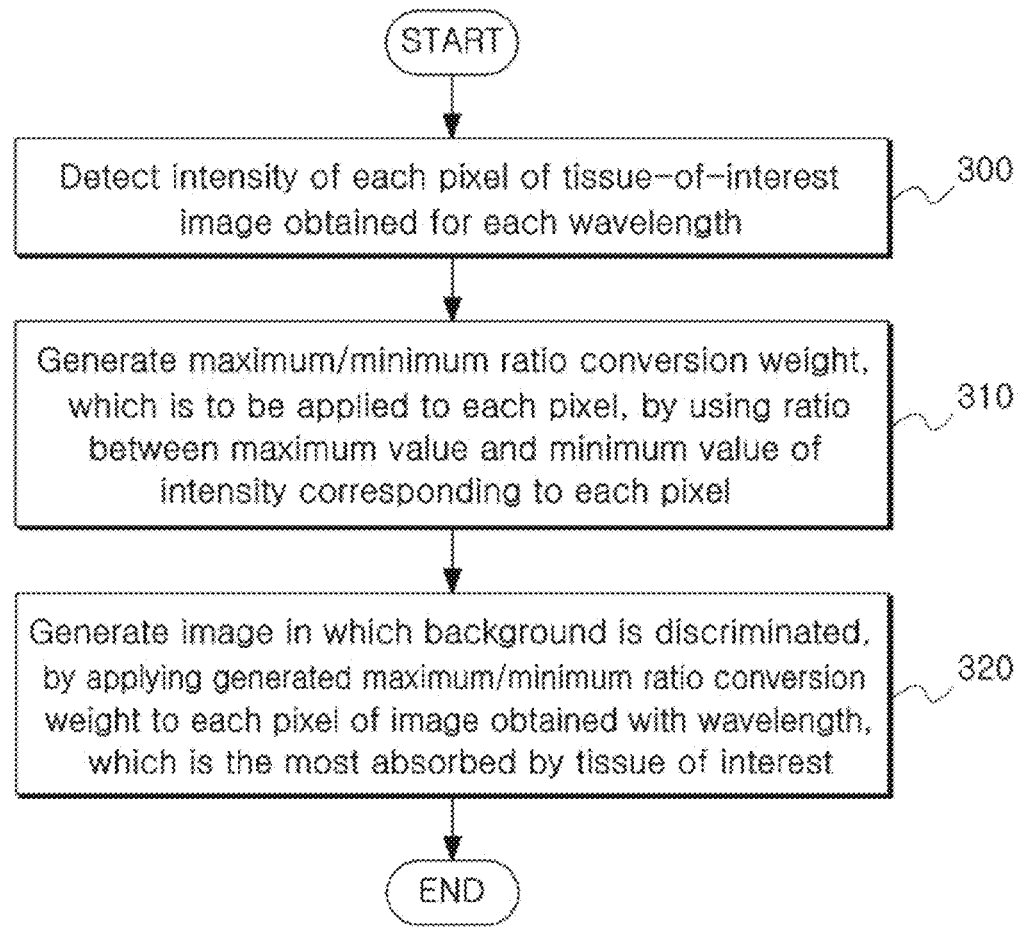
FIG. 6 is a flowchart for illustrating a method for discriminating a tissue of interest according to another preferred embodiment of the present disclosure.

FIG. 6 is a flowchart for illustrating a method for discriminating a tissue of interest according to another preferred embodiment of the present disclosure.

Referring to FIG. 6, a method for discriminating a tissue of interest according to this embodiment includes processes time-sequentially performed by the apparatus for discriminating a tissue of interest, depicted in FIG. 2. Therefore, even though not described in detail below, the features described above in relation to the apparatus for discriminating a tissue of interest, depicted in FIG. 2, are also applied to the method for discriminating a tissue of interest according to this embodiment.

In Step 300, the apparatus for discriminating a tissue of interest detects an intensity of each pixel of a tissue-of-interest image obtained for wavelength.

In Step 310, the apparatus for discriminating a tissue of interest generates a maximum/minimum ratio conversion weight, which is to be applied to each pixel, by using a ratio of a maximum value and a minimum value of an intensity corresponding to each pixel.

In more detail, after a ratio of a maximum value and a minimum value of an intensity corresponding to each pixel is extracted, a maximum/minimum ratio conversion weight equal to or greater than 0 and equal to or smaller than 1 is generated according to a difference between the maximum value and the minimum value. For example, if a pixel may be determined as a pixel of the tissue of interest when the difference between the maximum value and the minimum value is great, a maximum value of the maximum/minimum ratio conversion weight is endowed, and if a pixel may be determined as a pixel of a background when the difference between the maximum value and the minimum value is small, a minimum value of the maximum/minimum ratio conversion weight may be endowed. Meanwhile, for a pixel of a tissue other than the tissue of interest or the background, a maximum/minimum ratio conversion weight between 0 and 1 may be endowed.

In Step 320, the apparatus for discriminating a tissue of interest generates an image in which a background is discriminated, by applying the generated maximum/minimum ratio conversion weight to each pixel an image obtained with a wavelength, which is the most absorbed by the tissue of interest.

Figure 7:
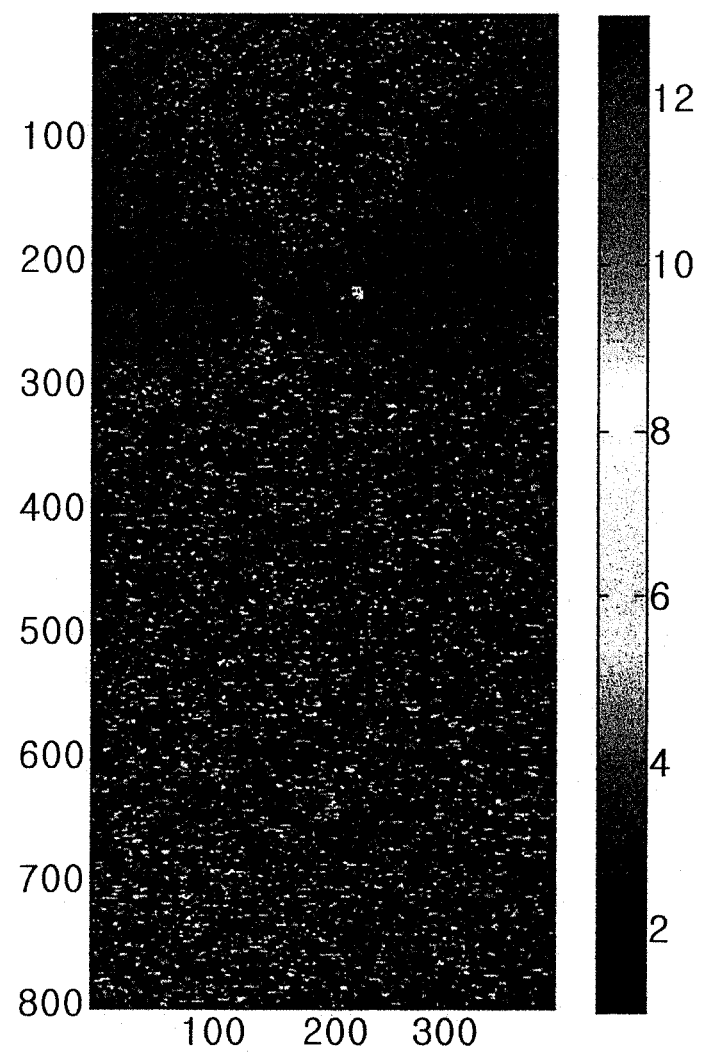
FIG. 7 shows an index frame generated by matching a color corresponding to an index of the index frame to each pixel.

FIG. 7 shows an index frame generated by matching a color corresponding to an index of the index frame to each pixel.

Figure 8:
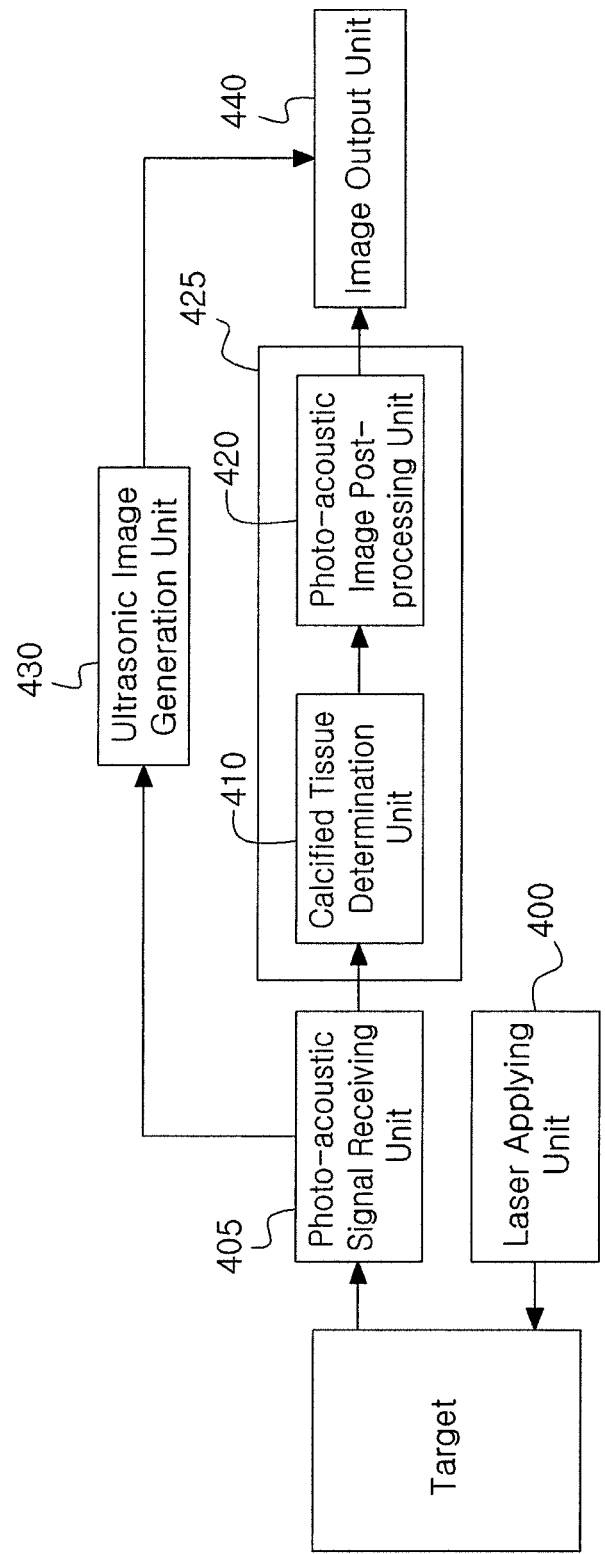
FIG. 8 is a diagram showing a photo-acoustic image (PAI) apparatus according to a preferred embodiment of the present disclosure.

FIG. 8 is a diagram showing a photo-acoustic image (PAI) apparatus according to a preferred embodiment of the present disclosure.

Referring to FIG. 8, a photo-acoustic image apparatus includes a laser applying unit 400, a photo-acoustic signal receiving unit 405, a photo-acoustic image generation unit 425, an ultrasonic image generation unit 430, and an image output unit 440. The photo-acoustic image generation unit 425 includes a calcified tissue determination unit 410 and a photo-acoustic image post-processing unit 420.

The laser applying unit 400 applies laser to a target which is to be observed.

The photo-acoustic signal receiving unit 405 receives a photo-acoustic signal generated after laser is applied to the target.

The calcified tissue determination unit 410 compares a magnitude of a photo-acoustic signal according to a wavelength of the laser and determines whether the tissue is a calcified tissue or a surrounding tissue.

The photo-acoustic image post-processing unit 420 emphasizes an image which is determined as a calcified tissue and removes an image which is determined as a surrounding tissue.

The ultrasonic image generation unit 430 generates an ultrasonic image by using the photo-acoustic signal received from the photo-acoustic signal receiving unit 405.

The image output unit 440 outputs a post-processed image from the photo-acoustic image post-processing unit 420 or outputs ultrasonic images generated by the post-processed image and the ultrasonic image generation unit 430 simultaneously.

Figure 9:
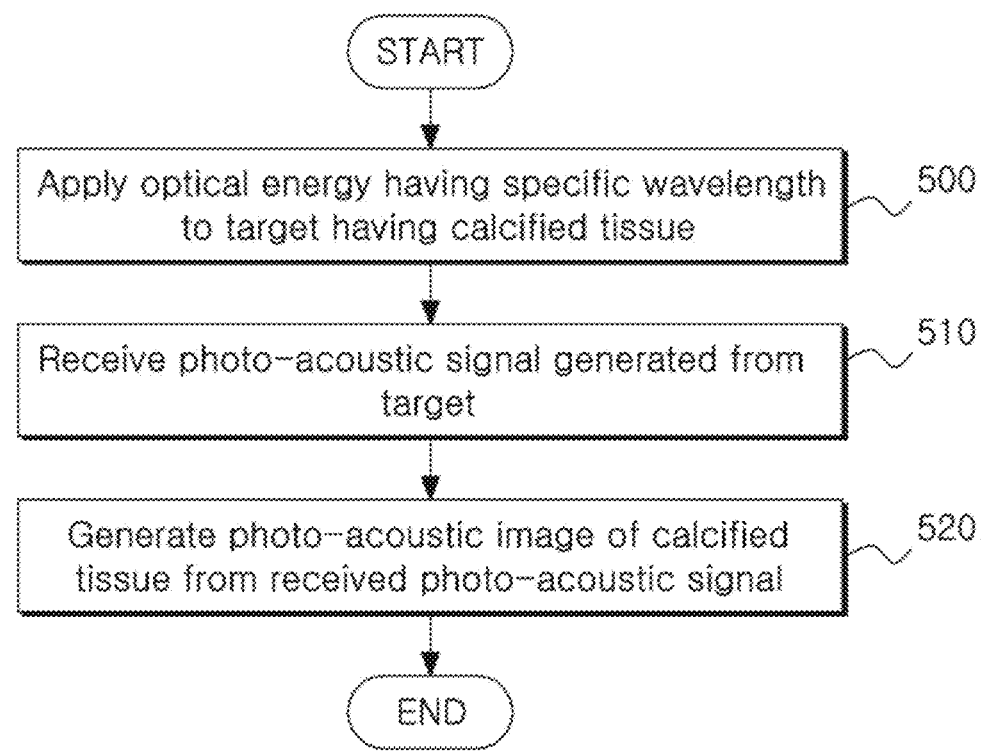
FIG. 9 is a flowchart for illustrating a photo-acoustic image method according to a preferred embodiment of the present disclosure.

FIG. 9 is a flowchart for illustrating a photo-acoustic image method according to a preferred embodiment of the present disclosure.

Referring to FIG. 9, a photo-acoustic image method according to this embodiment includes processes time-sequentially performed by the PIA apparatus, depicted in FIG. 8. Therefore, even though not described in detail below, the features described above in relation to the PIA apparatus, depicted in FIG. 8, are also applied to the photo-acoustic image method according to this embodiment.

In step 500, the photo-acoustic image apparatus applies optical energy having a specific wavelength to a target having calcified tissue.

In step 510, the photo-acoustic image apparatus receives a photo-acoustic signal generated from the target.

In step 520, the photo-acoustic image apparatus generates a photo-acoustic image of the calcified tissue from the photo-acoustic signal.

Figure 10:
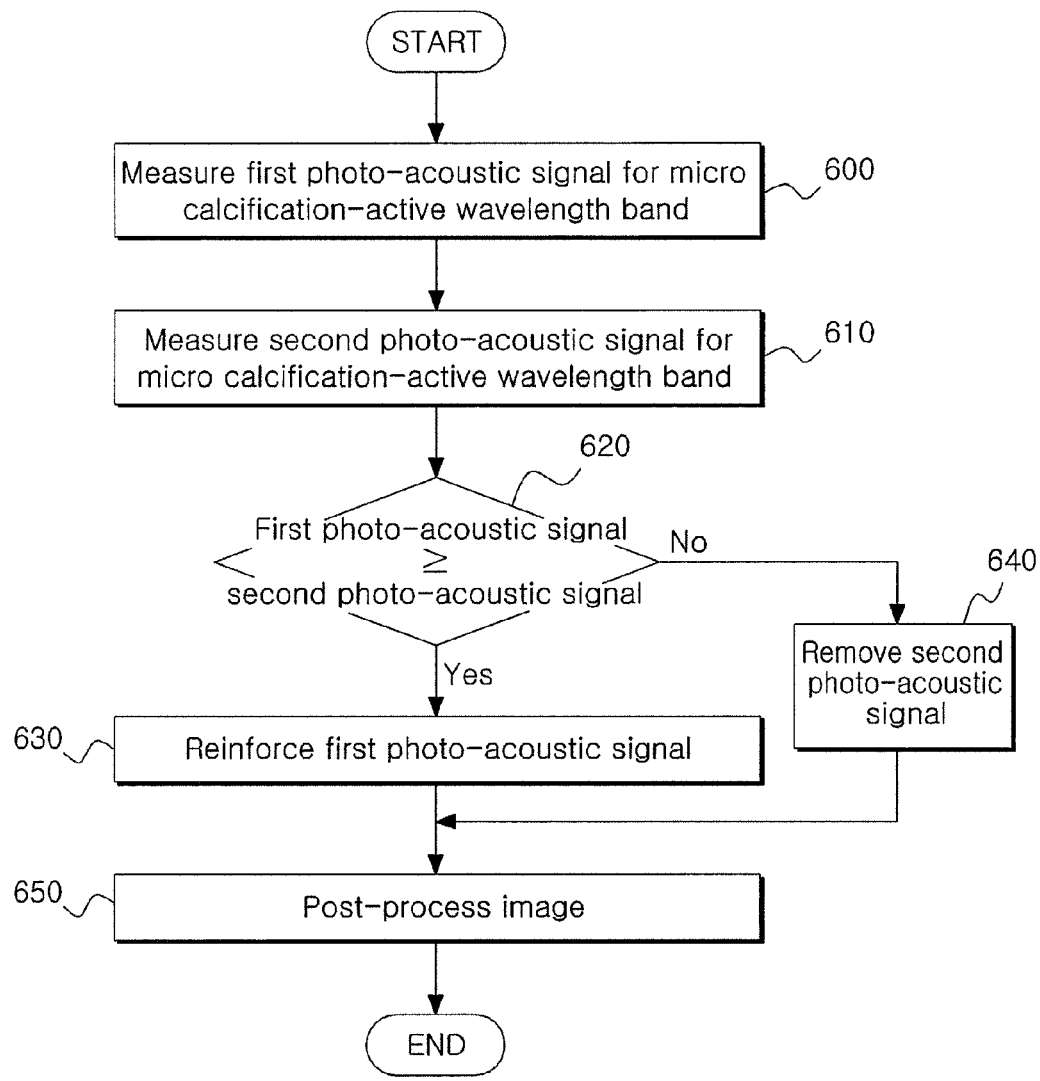
FIG. 10 is a detailed flowchart for illustrating Steps 510 and 520 of the photo-acoustic image method according to a preferred embodiment of the present disclosure, depicted in FIG. 9.

FIG. 10 is a detailed flowchart for illustrating Steps 510 and 520 of the photo-acoustic image method according to a preferred embodiment of the present disclosure, depicted in FIG. 9.

In step 600, the photo-acoustic image apparatus applies energy of a micro calcification-active wavelength band to a target to receive a first photo-acoustic signal.

At this time, the micro calcification-active wavelength band may be determined as a wavelength band when a magnitude of a photo-acoustic signal generated from the calcified tissue is greater than a first threshold.

In step 610, the photo-acoustic image apparatus may apply energy of a micro calcification-inactive wavelength band to the target to receive a second photo-acoustic signal.

At this time, the micro calcification-inactive wavelength band may be determined as a wavelength band when a magnitude of a photo-acoustic signal generated from the calcified tissue is smaller than a second threshold.

In step 620, the photo-acoustic image apparatus determines whether the first photo-acoustic signal is greater than the second photo-acoustic signal. If the first photo-acoustic signal is equal to or greater than the second photo-acoustic signal, the process proceeds to Step 630. If the first photo-acoustic signal is smaller than the second photo-acoustic signal, the process proceeds to Step 640.

In step 630, the photo-acoustic image apparatus determines that the target is a calcified tissue and reinforces the first photo-acoustic signal.

In step 640, the photo-acoustic image apparatus determines that the target is a surrounding tissue and removes the second photo-acoustic signal.

In step 650, the photo-acoustic image apparatus performs image post-processing to generate a final photo-acoustic image by using the reinforced first photo-acoustic signal and the removed second photo-acoustic signal.

Figure 11:
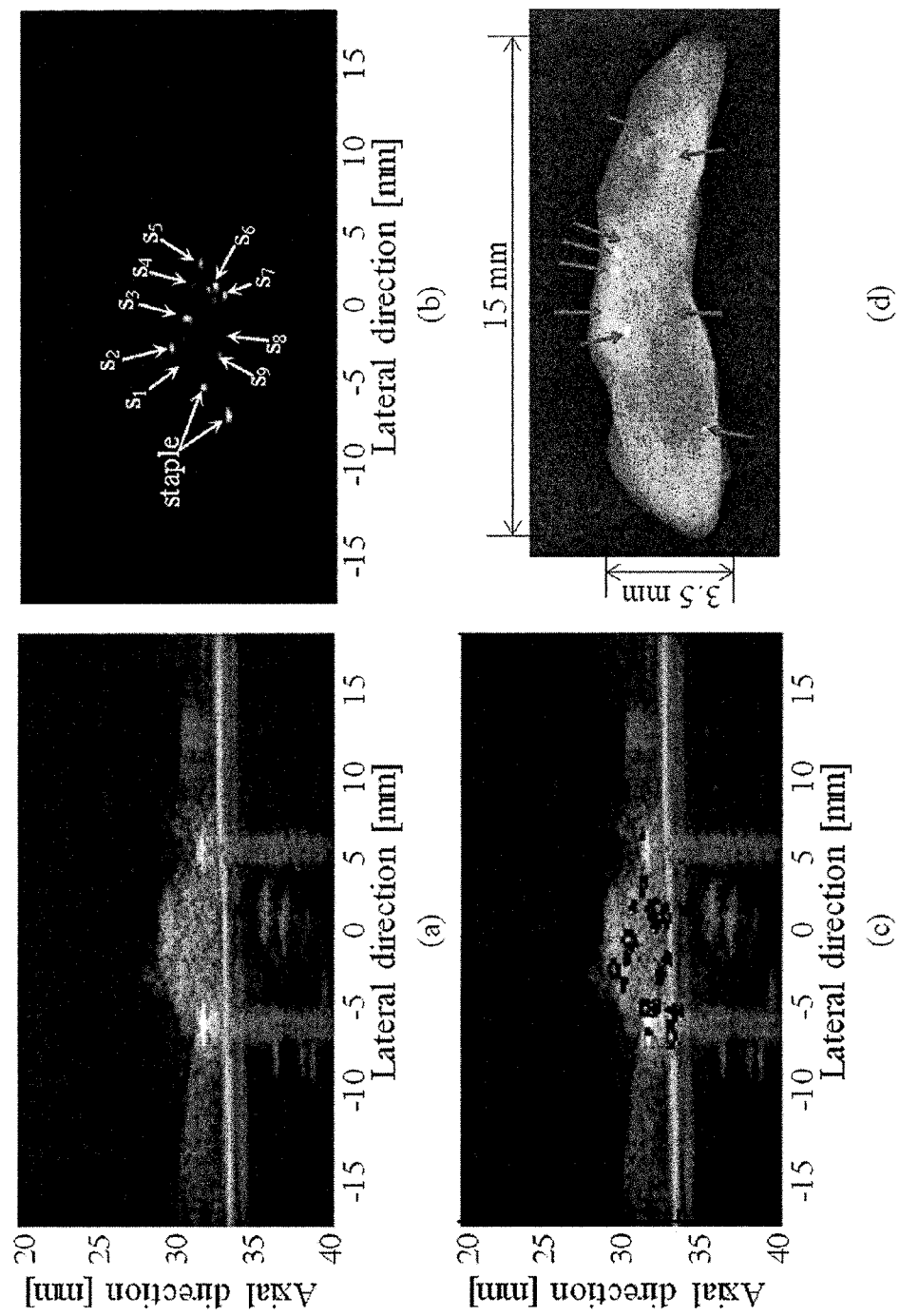
FIGS. 11a, 11b, 11c and 11d show a result of an ex vivo experiment for biological tissue specimen.

FIG. 11 shows a result of an ex vivo experiment for a biological tissue specimen.

FIG. 11(a) shows an ultrasonic image, FIG. 11(b) shows a photo-acoustic image, FIG. 11(c) shows a fused image of a photo-acoustic image and an ultrasonic image, and FIG. 11(d) shows a mammography image.

In the ultrasonic image depicted in FIG. 11(a), a micro-calcified tissue is not easily observed due to a low contrast. Meanwhile, the photo-acoustic image depicted in FIG. 11(b) is an image from which a calcified tissue reacting with an incident laser of an optimal wavelength is detected. Different from the ultrasonic image of FIG. 11(a), a calcified tissue is clearly observed in the photo-acoustic image of FIG. 11(b).

The photo-acoustic image depicted in FIG. 11(b) may clearly distinguish a difference between a calcified tissue and an existing surrounding tissue, and all micro-calcified tissues may be discriminated in the mammography image depicted in FIG. 11(d).

In the fused image of FIG. 11(c), an ultrasonic image and a photo-acoustic image are displayed to overlap with each other, which is helpful for finding a location of a calcified tissue.

Figure 12:
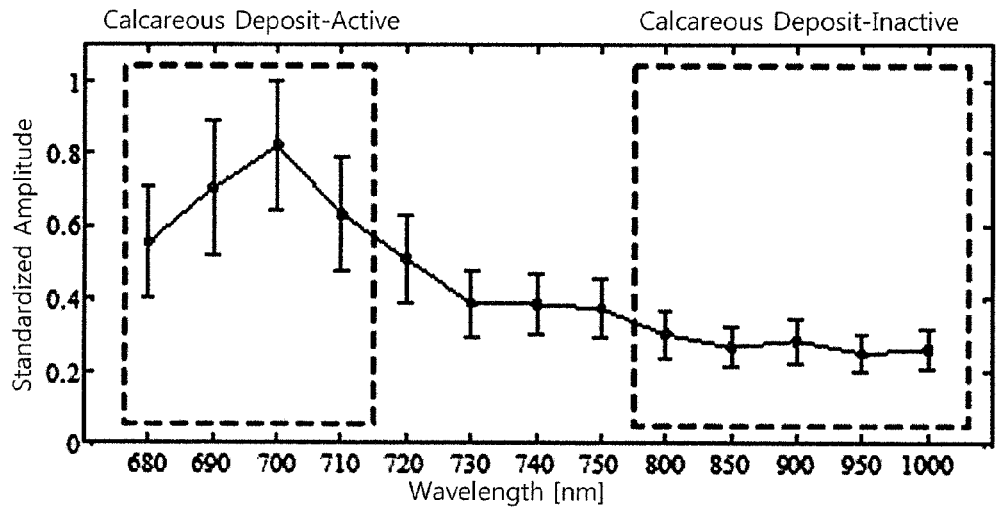
FIG. 12 shows a magnitude of a photo-acoustic signal generated according to a wavelength of laser, a micro calcification-active wavelength region and a micro calcification-inactive wavelength region.

FIG. 12 shows a magnitude of a photo-acoustic signal generated according to a wavelength of laser, a calcification-active wavelength region and a micro calcification-inactive wavelength region.

Referring to FIG. 12, in an ex vivo experiment, it can be found that a maximum magnitude of the photo-acoustic signal generated from the micro-calcified tissue is generated in a laser wavelength range of 680 nm to 710 nm.

In FIG. 12, optimal wavelengths at which photo-acoustic signals are generated to the maximum for seven breast tissue specimens are recorded, and their average and standard deviation are obtained. In each experiment, data was collected 16 times. The photo-acoustic image is optimal when optical energy has a wavelength of 680 nm to 710 nm, and in a wavelength range of 800 to 1000 nm, there is a small reaction, and thus the signal becomes so small not to be observed by naked eyes in the image.

Therefore, by contrasting reactions of a micro calcification-active wavelength band (680 to 710 nm) and a micro calcification-inactive wavelength band (800 to 1000 nm) classified by a wavelength band, an apparent form of the micro calcification may be confirmatively provided to the user.

In the present disclosure, for effective imaging of micro calcification and enhancing contrast with surrounding tissues, the degree of occurrence of photo-acoustic signal is compared between the micro calcification-active wavelength band and the micro calcification-inactive wavelength band of FIG. 12 to remove a background image and amplify a calcified tissue signal.

Figure 13:
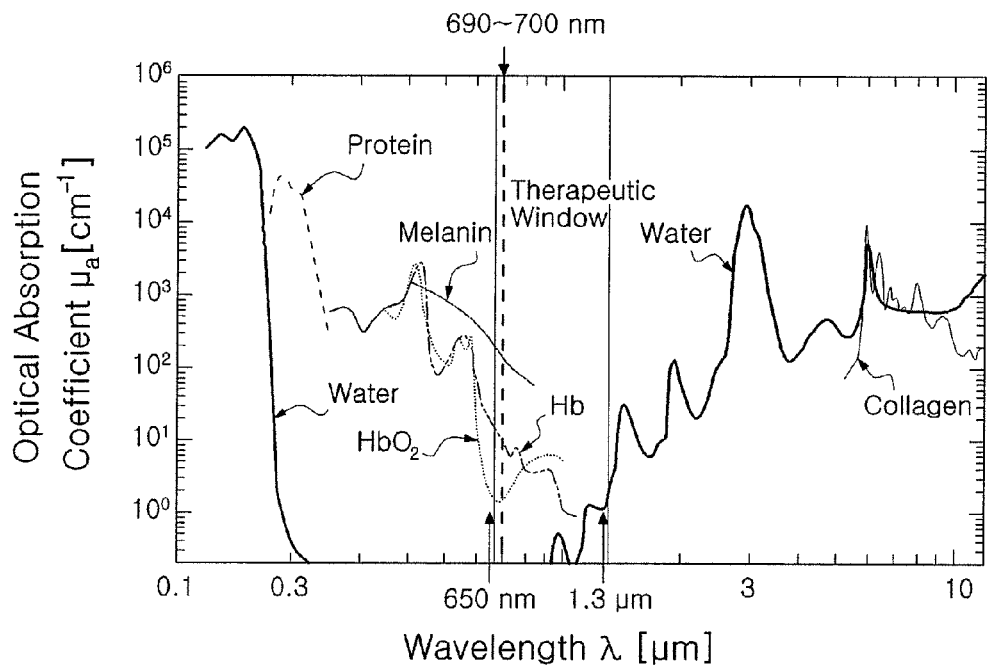
FIG. 13 shows a relation between a laser wavelength and an optical absorption coefficient ($\mu_a$) of each tissue.

FIG. 13 shows a relation between a laser wavelength and an optical absorption coefficient ($\mu_a$) of each tissue.

Optical energy of short pulses is applied to molecules, a photo-acoustic signal is acquired due to thermal expansion of a tissue caused by the optical energy, and an image is acquired by receiving the photo-acoustic signal. In this process, a tissue reacting thereto changes according to a wavelength of the applied optical energy, and it is possible to perform functionally discriminated molecule imaging by using the above. If reactions of various wavelengths of micro calcification are compared by using the above feature, a calcified tissue and a surrounding tissue may be discriminated in breast and thyroid tissues.

The absorption spectrum is a function of a laser wavelength, and different reactions are found at each tissue depending on the laser wavelength. A relation of an optical absorption coefficient of each wavelength in each tissue is depicted in FIG. 13, and this allows functional imaging. In other words, different molecules such as hemoglobin bonded to oxygen and hemoglobin dissociated from oxygen in blood show different absorption spectrum characteristics when reacting with incident laser, and thus functional imaging is available.

If a laser pulse with a peak absorption wavelength is irradiated, a molecule corresponding to the wavelength absorbs laser energy to the maximum and is converted into heat.

If the laser pulse width is shorter than a heat transfer time of the absorption energy, which is defined as thermal confinement, the absorption energy causes transitional thermoelastic expansion. Therefore, a photo-acoustic signal detected in an ultrasonic form may be generated and imaged.

As a result, the photo-acoustic image apparatus may image a micro-calcified tissue under the condition that an absorption spectrum of a micro-calcified tissue is known.

From the above condition, a specific wavelength of the laser pulse may be determined, and a greatest photo-acoustic signal in the micro-calcified tissue may be generated greater than the surrounding tissue.

In the present disclosure, an optimal laser wavelength is indirectly checked through an experiment, instead of measuring an absorption spectrum characteristic of the micro-calcified tissue.

By changing a wavelength in the range of 680 nm to 1000 nm, a magnitude of a photo-acoustic signal generated by an ex vivo experiment using a breast cancer specimen including a calcified tissue of a patient may be measured.

An intensity of a photo-acoustic signal generated from a target molecule is proportional to an amount of energy absorbed by the target molecule.

Total absorption energy may be expressed as Equation 2 below. Therefore, a magnitude of a generated photo-acoustic signal varies depending on an optical absorption coefficient of the corresponding tissue.

$$\text{Energy}_{total\ absorption} = \Gamma \mu_a F \qquad \text{Equation 2}$$

where $\Gamma$ represents a dimensionless Gruneisen parameter, $\mu_a$ represents an optical absorption coefficient, F and an optical fluence (J/m$^2$) of an absorber.

After the target absorbs laser energy, a photo-acoustic signal is generated and propagated through a medium, which may be expressed as Equation 3 below.

$$\left(\nabla^2 - \frac{1}{v_s^2}\frac{\partial^2}{\partial t^2}\right)p = -\frac{\Gamma}{v_s^2}\frac{\partial H}{\partial t} \qquad \text{Equation 3}$$

where p represents a negative pressure, $v_s$ represents a longitudinal wave velocity in a medium, t represents time, and H represents a heating function showing heat energy stored per unit volume and unit time.

In addition, $\Gamma$ may be expressed as Equation 4 below.

$$\Gamma = \frac{\beta v_s^2}{C_p} \qquad \text{Equation 4}$$

where $\beta$ represents a volume expansion heat coefficient, and $C_p$ represents a thermal capacity at a specific negative pressure.

In order to obtain an optical absorption coefficient ($\mu_a$) by using the above equations, F and $\Gamma$ should be constantly maintained. If an incident energy density is fixed, F may be considered as a constant, and $\Gamma$ may also be considered as a constant by maintaining temperature of the medium constantly even though temperature increases after absorbing energy of the irradiated laser.

Therefore, under the above conditions, namely if an ambient temperature and an amount of applied energy are fixed, F and r are fixed, and the amount of energy observed by the target depends on $\mu_a$. Therefore, a magnitude of the photo-acoustic signal is directly proportional to $\mu_a$ of the micro-calcified tissue. $\mu_a$ is used for determining a characteristic of the absorption spectrum, and an indirect method is used for determining an optimal laser wavelength.

Meanwhile, a generated photo-acoustic pressure is beam-focused through an ultrasonic transducer, and a greatest photo-acoustic signal is recorded. In this case, it is desirable to perform beam focusing several times and then use their average and standard deviation.

If reactions of seven calcified tissues are observed and then an average and standard deviation of photo-acoustic signals are obtained, it can be found that the calcified tissue shows a greatest photo-acoustic signal in the wavelength range of 680 nm to 710 nm.

This means that a photo-acoustic signal tends to show a maximum value at a wavelength having low reaction in other skins and internal biological tissues, which has effectiveness in actual human tissue imaging.

Referring to FIG. 13 again, a therapeutic window serving as a wavelength band with low reaction in other skins and internal biological tissues is shown in a wavelength range of 0.65 to 1.3 µm.

Figure 14:
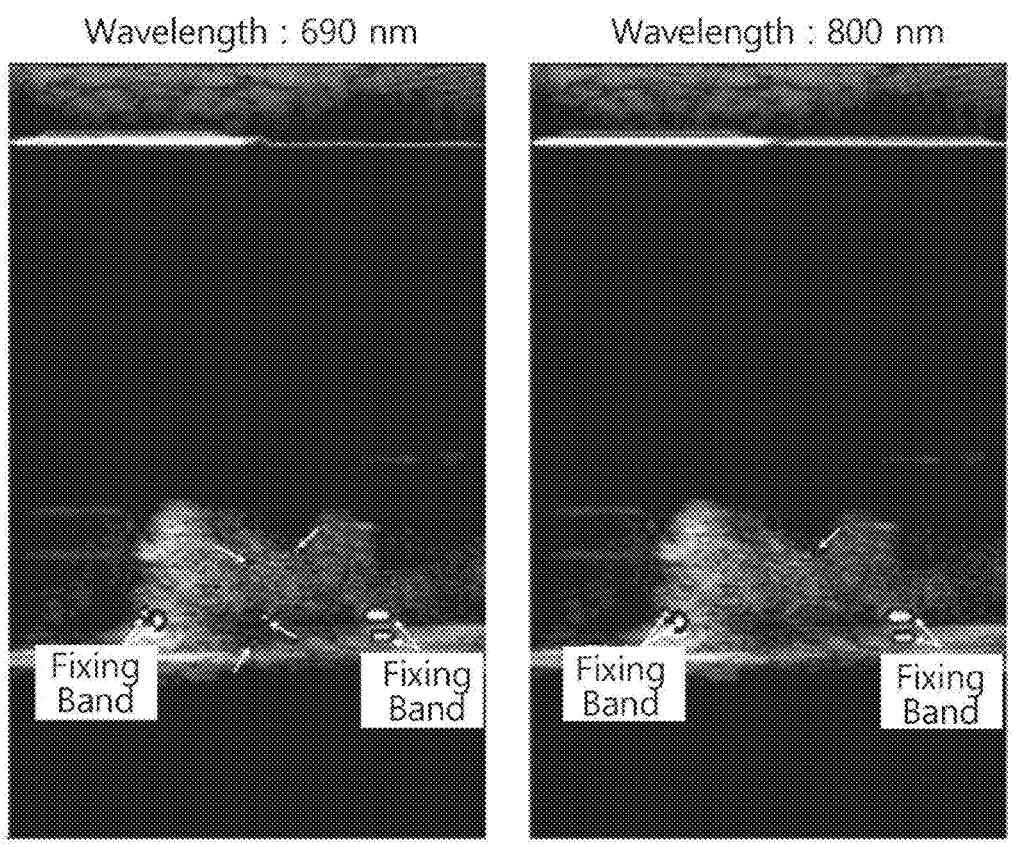
FIG. 14 is a diagram comparatively showing a photo-acoustic image when a laser with a wavelength of 690 nm is applied to a target with a photo-acoustic image when a laser with a wavelength of 800 nm is applied to the target.

FIG. 14 is a diagram comparatively showing a photo-acoustic image when a laser with a wavelength of 690 nm is applied to a target with a photo-acoustic image when a laser with a wavelength of 800 nm is applied to the target.

When laser with a wavelength of 690 nm is applied to a target, a photo-acoustic image shows signals coming from four micro-calcified tissues and a fixing band for fixing a specimen.

Meanwhile, when laser with a wavelength of 800 nm is applied to a target, in the photo-acoustic image, the signal of the fixing band is expressed without any change, compared with the case where the wavelength is 690 nm, but among four signals coming from micro calcification, just one signal is generated. In this case, this is not micro calcification and is removed from the image.

Signals simultaneously expressed in the image of 690 nm and the image of 800 nm may be removed, and only the other three micro calcification signals may be provided to a user.

A range compared with the wavelength range of 680 nm to 710 nm may vary depending on a surrounding tissue of the calcified tissue. A wavelength band capable of reducing reacting photo-acoustic signals around a tissue, where the calcified tissue is present, to the minimum may be used as a comparable range.

In case of the breast or thyroid, the comparable range may be determined between 800 nm and 1200 nm. At this time, a wavelength band having a photo-acoustic magnitude equal to or smaller than 50% of the photo-acoustic magnitude of the wavelength band of 680 nm to 710 nm may be determined as a comparative band.

The method for operating the stimulation apparatus or the electrical stimulation device may be implemented as an application or program commands executable by various kinds of computer means and recorded on a computer-readable recording medium. The computer-readable recording medium may include program commands, data files, data structures or the like solely or in combination. The program commands recorded on the medium may be specially designed or configured for the present disclosure or known to and available by computer software engineers. The computer-readable recording medium includes, for example, magnetic media such as a hard disk, a floppy disk and a magnetic tape, optical media such as CD-ROM and DVD, magneto-optical media such as a floptical disk, hardware devices such as ROM, RAM and a flash memory, specially configured to store and perform program commands, or the like. The program commands include not only machine codes made by a complier but also high-level language codes executable by a computer by using an interpreter. The hardware device may be configured to operate as at least one software module to perform the operations of the present disclosure, or vice versa.

While the exemplary embodiments have been shown and described, it will be understood by those skilled in the art that various changes in form and details may be made thereto without departing from the spirit and scope of this disclosure as defined by the appended claims. In addition, many modifications can be made to adapt a particular situation or material to the teachings of this disclosure without departing from the essential scope thereof.

Therefore, the spirit of the present disclosure should not be limited to the embodiments described above, and the appended claims and their equivalents or modifications should also be regarded as falling within the scope of the present disclosure.

The invention claimed is:

1. A method for discriminating a tissue of interest, comprising:
    detecting an intensity of each pixel of a tissue-of-interest image obtained for a plurality of wavelengths;
    matching an index corresponding to an image, which has a greatest intensity corresponding to each pixel, to each pixel;
    generating a signal weight corresponding to each pixel in consideration of a wavelength absorbed by the tissue of interest;
    applying the generated signal weight of each pixel to each pixel of an image obtained with a wavelength, which is the most absorbed by the tissue of interest; and
    generating an image in which the tissue of interest is discriminated.

2. The method for discriminating a tissue of interest according to claim 1,
    wherein, in said generating of a signal weight, a signal weight of a pixel corresponding to an index of a wavelength, at which an optical absorption coefficient of the tissue of interest and an optical absorption coefficient of a surrounding tissue are the most different from each other, is selected as a greatest value.

3. The method for discriminating a tissue of interest according to claim 1,
    wherein a signal weight of a pixel corresponding to an index of a wavelength, at which a difference between an optical absorption coefficient of the tissue of interest and an optical absorption coefficient of a surrounding tissue is maximum, is selected as a greatest value even though the index is not an index of a wavelength at which optical energy is the most absorbed by the tissue of interest.

4. The method for discriminating a tissue of interest according to claim 1,
    wherein a signal weight of a pixel corresponding to an index of a wavelength, which is the most absorbed by the tissue of interest, is selected as a greatest value.

5. The method for discriminating a tissue of interest according to claim 1, wherein a signal weight of a pixel corresponding to an index of a wavelength, which is the second most absorbed by the tissue of interest, is set to be equal to or greater than 0 and smaller than a signal weight of the pixel corresponding to the index of a wavelength, which is the most absorbed by the tissue of interest.

6. A method for discriminating a tissue of interest, comprising:
    detecting an intensity of each pixel of a tissue-of-interest image obtained for a plurality of wavelengths;
    generating a maximum/minimum ratio conversion weight, which is to be applied to each pixel, by using a ratio between a maximum value and a minimum value of the intensity corresponding to each pixel;
    applying the generated maximum/minimum ratio conversion weight to each pixel of an image obtained with a wavelength, which is the most absorbed by the tissue of interest; and
    generating an image in which a background is discriminated.

7. The method for discriminating a tissue of interest according to claim 6,
    wherein, when a difference between the maximum value and the minimum value is greater than a predetermined value, the pixel is determined as a pixel of the tissue of interest and a maximum value of the maximum/minimum ratio conversion weight is endowed, and when the difference between the maximum value and the minimum value is smaller than the predetermined value, the pixel is determined as a background and a minimum value of the maximum/minimum ratio conversion weight is endowed.

8. A method for discriminating a tissue of interest, comprising:

detecting an intensity of each pixel of a tissue-of-interest image obtained for a plurality of wavelengths;

matching an index corresponding to an image, which has a greatest intensity corresponding to each pixel, to each pixel;

generating a signal weight corresponding to each pixel in consideration of a wavelength absorbed by the tissue of interest;

generating a maximum/minimum ratio conversion weight, which is to be applied to each pixel, by using a ratio between a maximum value and a minimum value of the intensity corresponding to each pixel;

generating a final weight by using the signal weight and the maximum/minimum ratio conversion weight;

applying the generated final weight of each pixel to each pixel of an image obtained with a wavelength, which is the most absorbed by the tissue of interest; and generating an image in which a background is discriminated.

9. A non-transitory computer-readable recording medium, in which a program for executing the method defined in claim 1 in a computer is recorded.

10. An apparatus for discriminating a tissue of interest, comprising:

a pixel intensity detection unit configured to detect an intensity of each pixel of a tissue-of-interest image obtained for each wavelength;

an index frame generation unit configured to match an index corresponding to an image, which has a greatest intensity corresponding to each pixel, to each pixel to generate an index frame;

a signal weight generation unit configured to generate a signal weight corresponding to each pixel in consideration of a wavelength absorbed by the tissue of interest;

a weight applying unit configured to-apply the generated signal weight of each pixel to each pixel of an image obtained with a wavelength, which is the most absorbed by the tissue of interest, and to generate an image in which a background is discriminated, wherein each of the pixel intensity detection unit, the index frame generation unit, the signal weight generation unit, and the weight applying unit are implemented by one or more processor.

11. An apparatus for discriminating a tissue of interest, comprising:

a pixel intensity detection unit configured to detect an intensity of each pixel of a tissue-of-interest image obtained for each wavelength;

a maximum/minimum ratio conversion weight generation unit configured to generate a maximum/minimum ratio conversion weight, which is to be applied to each pixel, by using a ratio between a maximum value and a minimum value of the intensity corresponding to each pixel;

a weight applying unit configured to apply the generated maximum/minimum ratio conversion weight to each pixel of an image obtained with a wavelength, which is the most absorbed by the tissue of interest, and to generate an image in which a background is discriminated, wherein each of the pixel intensity detection unit, the maximum/minimum ratio conversion weight generation unit and the weight applying unit are implemented by one or more processor.

12. An apparatus for discriminating a tissue of interest, comprising:

a pixel intensity detection unit configured to detect an intensity of each pixel of a tissue-of-interest image obtained for each wavelength;

an index frame generation unit configured to match an index corresponding to an image, which has a greatest intensity corresponding to each pixel, to each pixel to generate an index frame;

a signal weight generation unit configured to generate a signal weight corresponding to each pixel in consideration of a wavelength absorbed by the tissue of interest;

a maximum/minimum ratio conversion weight generation unit configured to generate a maximum/minimum ratio conversion weight, which is to be applied to each pixel, by using a ratio between a maximum value and a minimum value of the intensity corresponding to each pixel;

a weight frame generation unit configured to generate a final weight by using the signal weight and the maximum/minimum ratio conversion weight to generate a weight frame; and a weight applying unit configured to apply the generated final weight of each pixel to each pixel of an image obtained with a wavelength, which is the most absorbed by the tissue of interest, and to generate an image in which a background is discriminated, wherein each of the pixel intensity detection unit, the index frame generation unit, the signal weight generation unit, the maximum/minimum ratio conversion weight generation unit, the weight frame generation unit and the weight applying unit are implemented by one or more processor.

* * * * *